United States Patent
Seguin

(10) Patent No.: US 8,822,433 B2
(45) Date of Patent: Sep. 2, 2014

(54) COMPLEX COMBINING AN ORGANIC SILICON DERIVATIVE WITH HYALURONIC AND ACID CALIBRATED FRAGMENTS, FOR PREVENTIVE AND REPAIRING ACTION OF CUTANEOUS DAMAGES

(71) Applicant: Exsymol S.A.M., Monaco (MC)

(72) Inventor: Marie-Christine Seguin, Monaco (MC)

(73) Assignee: Exsymol S.A.M., Monaco (MC)

( * ) Notice: Subject to any disclaimer, the term of this patent is extended or adjusted under 35 U.S.C. 154(b) by 0 days.

(21) Appl. No.: 13/649,640

(22) Filed: Oct. 11, 2012

(65) Prior Publication Data
US 2013/0035308 A1  Feb. 7, 2013

Related U.S. Application Data

(62) Division of application No. 12/572,658, filed on Oct. 2, 2009, now abandoned.

(30) Foreign Application Priority Data

Oct. 3, 2008  (FR) ...................... 08 05479

(51) Int. Cl.
*A61K 31/728* (2006.01)
*C07F 7/08* (2006.01)
*C08B 37/00* (2006.01)
*A61K 8/73* (2006.01)
*A61K 31/695* (2006.01)
*C08B 37/08* (2006.01)
*A61K 8/58* (2006.01)
*A61Q 19/08* (2006.01)

(52) U.S. Cl.
CPC ............... *A61K 8/735* (2013.01); *A61K 31/695* (2013.01); *C08B 37/0072* (2013.01); *A61K 31/728* (2013.01); *C07F 7/0836* (2013.01); *A61K 8/585* (2013.01); *A61Q 19/08* (2013.01)
USPC ............... 514/63; 514/54; 536/55.1; 556/463

(58) Field of Classification Search
None
See application file for complete search history.

(56) References Cited

U.S. PATENT DOCUMENTS

| 5,037,803 A | 8/1991 | Gueyne et al. |
| 2007/0172442 A1 | 7/2007 | Saurat et al. |

FOREIGN PATENT DOCUMENTS

| GB | 2159408 | 12/1985 |
| WO | 2005082421 | 9/2005 |

OTHER PUBLICATIONS

Malle et al., "Very Low Molecular Weight Hyaluronic Acid for Antiaging and Antiwrinkle Treatment," http://web.archive.org/web/20080129193022/biopolymer.novozymes.com, (Jan. 29, 2008).
Hascall et al., "Hyaluronan: Structure and Physical Properties," http://www.glycoforum.gr.jp/science/hyaluronan/hyaluronanE.html., Jun. 1, 2010, pp. 1-10.
Asari, A., "Novel functions of Hyaluronan Oligosaccharides," http://www.glycoforum.gr.jp/science/hyaluronan/hyaluronanE.html., Jun. 1, 2010, pp. 1-9.
Noble, P., "Hyaluronan and its catabolic products in tissue injury and repair," Matrix Biology, 21 (2002) 25-29.
Stern et al., "Hyaluronan in skin: aspects of aging and its pharmacologic modulation," Clinics in Dermatology, (2008) 26, 106-122.
Tchorzewski, K., "Hyaluronan-mediated regulation of inflammation," Postepy Hig Med Dosw (Online) Nov. 19, 2007; 61:683-689 (Abstract only).
Kaya et al., "Hyaluronate Fragments Reverse Skin Atrophy by a CD44-Dependent Mechanism," PLoS Medicine, Dec. 2006, vol. 3, Issue 12/e493, pp. 2291-2303.
Tammi et al., "Degradation of Newly Synthesized High Molecular Mass Hyaluronan in the Epidermal and Dermal Compartments of Human Skin in Organ Culture," The Journal of Investigative Dermatology, vol. 97, No. 1, Jul. 1991, pp. 126-130.
Brown et al., "Absorption of Hyaluronan Applied to the Surface of Intact Skin," The Journal of Investigative Dermatology, vol. 113, No. 5, Nov. 1999, pp. 740-746.
Meyer et al., "Age-Dependent changes of Hyaluronan in Human Skin," The Journal of Investigative Dermatology, vol. 102, No. 3, Mar. 1994, pp. 385-389.
Fioravanti et al., "Effect of hyaluronic acid (MW 500-330 kDa) on proteoglycan and nitric oxide production in human osteoarthritic chondrocyte cultures exposed to hydrostatic pressure," OsteoArthritis and Cartilage (2005) 13, 688-696.
Brown, "Bond Valences—A Simple Structural Model for Inorganic Chemistry," Chem. Soc. Rev., (1978) 359-376.
Gove et al., Definition of prevent, Webster's Third New International Dictionary, (1963), 1798.
"Structural Improvement, Epidermosil® Sales Brochure by Exsymol (2013)".

*Primary Examiner* — Eric Olson
(74) *Attorney, Agent, or Firm* — Volpe and Koenig, P.C.

(57) ABSTRACT

The invention concerns a complex based on an organic silicon derivative. The invention is characterized in that said derivative is combined, by weak bonds, with one or several hyaluronic acid calibrated fragments of molecular weight comprised between 150 and 750 kDa, said derivative being of general formula (I): $R_xSi(OH)_{4-x}$, (I) wherein: R is a ($C_1$-$C_4$) alkyl, and x=1 or 2. The invention also concerns the use of such a complex in the prevention or the repair of cutaneous damages.

8 Claims, 1 Drawing Sheet

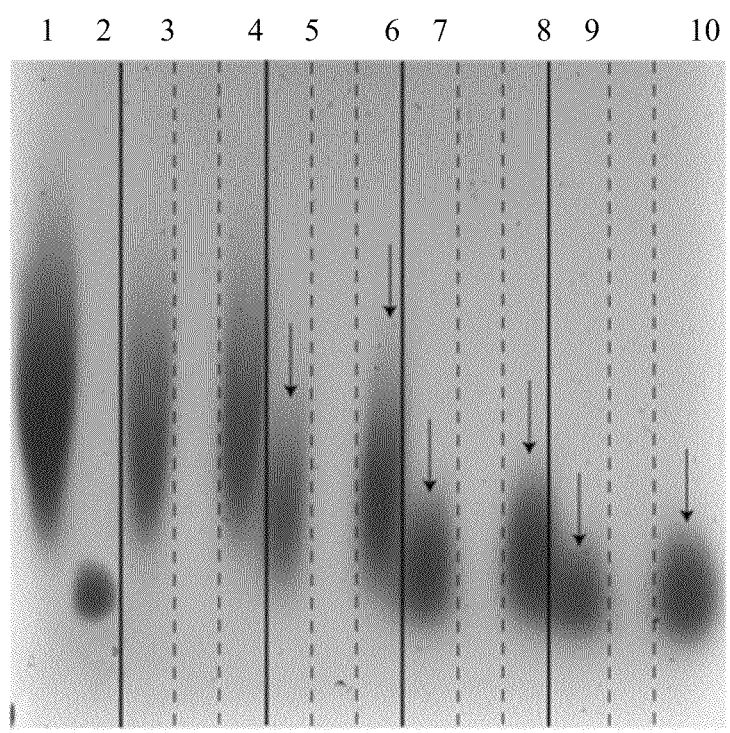

US 8,822,433 B2

COMPLEX COMBINING AN ORGANIC SILICON DERIVATIVE WITH HYALURONIC AND ACID CALIBRATED FRAGMENTS, FOR PREVENTIVE AND REPAIRING ACTION OF CUTANEOUS DAMAGES

This application is a Divisional of U.S. application Ser. No. 12/572,658 filed Oct. 2, 2009, which claims priority under 35 U.S.C. 119 to French application No. FR08/05479 filed Oct. 3, 2008, both of which are incorporated by reference herein as if fully set forth.

The invention concerns a complex combining an organic silicon derivative with one or several hyaluronic acid calibrated fragments, and its use in the prevention or the repair of cutaneous damages.

BACKGROUND

Linear polysaccharide constituted of repetitive units of D-glucuronic acid and N-acetyl-D-glucosamine, the hyaluronic acid is found in the extra-cellular matrix of numerous connective tissues (skin, tendons, muscles, etc), more precisely as a polyanion called "hyaluronane".

In the skin for instance, the hyaluronic acid (hereafter "HA") is one of the major components. An important amount is indeed found in the dermal and epidermal extra-cellular matrix. Its hydrophilic and viscoelastic properties make it an essential actor in the preservation of moisturizing, volume and cutaneous cohesion.

The HA synthesized by fibroblasts and keratinocytes (hereafter "native HA") mainly exists as polymers of very high molecular weight (>to 2.000 kDa) able even to reach 4.000 kDa with a chain of 10.000 disaccharides (Hascall V. C. and al., GlycoForum/Hyaluronan Today (1997), chapter 1).

However, the native HA is submitted in skin to a set of physiological damage reactions, notably enzymatic, called catabolism that aims at reducing it in smaller fragments (hereafter "fragmented HA"). Since several years, research teams turned their attention towards the catabolism of HA and its consequences in the organism. And the conclusion of all these works is in general unanimous, that is to say that the fragmented HA has a different behavior from the native HA, and that according to the size of fragments, in other words their molecular weight, it is observed different biological effects, and even opposite (Noble P. W., Matrix Biol. (2002), vol. 21, pp. 25-29; Asari A., GlycoForum/Hyaluronan Today (2005), chapter 29 and quoted references).

It is thus reported for HA fragments said of high molecular weight an effect on regeneration and healing, an important role as regulator of the inflammatory process, but also an immunosuppressive effect. On the other hand, oligomers said of low weight are presented as entities able to activate the immune cells and to deliver endogenous signals with respect to stress, but also to be powerful inducers of inflammation and angiogenesis (Stern R., Clin. Dermatol. (2008), vol. 26, pp. 106-122; Krasinski R. et al., Postepy Hig. Med. Dosw (2007), vol. 61, pp. 683-689).

More precisely concerning skin, it is reported a stimulation of the keratinocytes' proliferation in culture, for fragments called "of intermediate size" with a molecular weight between 50 and 400 kDa (Kaya G. and al., PLoS Medicine (2006), vol. 3, pp. 2291-2303). These effects are also observed after topical application of a preparation based on HA fragments of molecular weight between 50 and 750 kDa (described "of low molecular weight" in the specification of FR 2865651 application). This advantageous property, notably synonymous of a better barrier function of the skin with a thickness of the epidermis increased, would be however not anymore observed with small HA fragments lower than 50 kDa (Kaya G. and al., PLoS Medicine (2006), vol. 3, pp. 2291-2303).

Although it has been considered for a long time that a transcutaneous crossing of HA, for a benefit beyond the simple surface of the skin and the cornea layer, could be only considered for fragments of HA with very low molecular weight (< to 50 kDa, Tammi R. and al., J. Invest. Dermatol. (1991), vol. 97, pp. 126-130), it is henceforth mentioned a diffusion capacity in the epidermis for HA fragments of definitely higher size, namely for fragments from 360 to 400 kDa (Brown T. J. and al., J. Invest. Dermatol. (1999), vol. 113, pp. 740-746) or else for the above mentioned intermediate fragments (50-400 kDa). This diffusion would even go as far as able to reach the dermis with also the above referred topical preparation based on HA (50-750 kDa).

In the cosmetic area and especially the one combating cutaneous aging, it can be advisable to bring topically to the skin some fragmented hyaluronic acid with appropriate size, and this, in order to fight against aging effects or extrinsic factors (free radicals, ultra-violet radiation, pollution, etc). It is indeed admitted that aging or ultra-violet radiations influence the HA catabolism and the release of fragments, and can result in a lower intracellular production and a more uneven layout (Meyer and al., J. Invest. Dermatol. (1994), vol. 3, pp. 385-389). However, a cosmetic application would not satisfy with unwanted secondary effects, such as here-above mentioned pro-inflammatory effect for small fragments of hyaluronic acid.

BRIEF DESCRIPTION OF THE DRAWINGS

FIG. 1 illustrates an agarose gel. The gel displays, for the three times of sampling and reaction (5 min, 15 min and 30 min), a more important distribution of HA with a high molecular weight for the MSH complex according to the invention, compared to fragmented HA non combined. Lane 1 represents HA fragments of molecular weight between 150-600 kDa; lane 2 represents HA fragments of molecular weight <20 kDa; lane 3 represents HA fragments of molecular weight between 150-600 kDa+enzyme (0 min : reaction time); lane 4 represents MSH complex+enzyme (0 min : reaction time); lane 5 represents HA fragments of molecular weight between 150-600 kDa+enzyme (5 min : reaction time); lane 6 represents MSH complex+enzyme (5 min : reaction time); lane 7 represents HA fragments of molecular weight between 150-600 kDa+enzyme (15 min : reaction time); lane 8 represents MSH complex+enzyme (15 min : reaction time); lane 9 represents HA fragments of molecular weight between 150-600 kDa+enzyme (30 min : reaction time); and lane 10 represents MSH complex+enzyme (30 min : reaction time)

DETAILED DESCRIPTION

Therefore in the light of what precedes conjugated to the need of new products with the comfort of a topical application, the technical problem that intends to solve the invention is to develop a new active ingredient based on hyaluronic acid fragments, with the double purpose:
  to potentiate/increase the recognized biological effects to the hyaluronic acid fragments said of weak or medium molecular weight,
  to avoid the pro-inflammatory adverse effect of small fragments produced by the catabolic action of cutaneous tissues.

The applicant's choice settled on a molecular entity under the form of a complex, combining an organic silicon derivative with hyaluronic acid calibrated fragments of molecular weight between 150 and 750 kDa, this for both following reasons.

Firstly, the aforesaid complex represented an advantageous reply to previously expressed purposes, illustrated by:
- the evidence of a greatly superior cytostimulant effect on a reconstructed human epidermis model compared to the one observed for the same fragments of hyaluronic acid but not combined [see hereafter test 1], thus suggesting an effect of synergy between siliconed and hyaluronic parts of the complex.
- a real tolerance coming with this cellular renewal since it is not observed a significant induction of pro-inflammatory cytokines compared with the used control [see hereafter test 2]. This induction is even lowered for one of the tested cytokines.

Secondly, unexpectedly for the applicant, it has been observed during an in vitro study on the kinetic deterioration of HA fragments with hyaluronidases a lesser sensitivity and accessibility of these HA fragments to these enzymes as soon as these fragments happen to be combined as a complex with an organic silicon derivative [see hereafter test 3]. Indeed, in comparison with fragmented HA with same weight but not combined, an agarose gel electrophoresis evidenced the presence of a more important distribution of HA fragments with high molecular weight. Such a behavior is appreciable in the context of the invention, because it is the proof of a slowed down catabolism, also suggesting a protective role of the organic silicon derivative on HA fragments as a complex.

In the prior art, it is nevertheless to note a cosmetic product with $R_nSi(OR')_m(OR'')_p$ as formula combining an organo-silicon compound with a biologically active compound (R'), notably hyaluronic acid quoted as a non limitative instance, and a dermatophilic molecule (R'') whose role is to prevent the crossing of organic silicon in the subjacent tissues of skin (EP 0289366 patent). The R and R' radicals are however with large scope chosen among simple organic compounds with of one or several alcohol, phenol, acid, amino or amino-acid functions. In addition in this document and even if the hyaluronic acid is listed, it is not mentioned the use of HA fragments with calibrated size, nor a particular efficiency on the epidermal cellular renewal as observed with the present invention. The same remarks apply to organo-silicon compounds under solid form within EP 0867445 european patent application, as well as for the moisturizing product object of FR 2561915 application. In this French reference, it is proposed the combination of a silanol with a hydrosoluble substance clearly under the state of polymer, such as proteins, mucopolysaccharides, notably hyaluronic acid, or else cellulose derivatives, and this for the sole effect of humidity preservation and of sticky sensation absence on skin.

Thus, according to a first aspect, the invention has for object a complex based on an organic silicon derivative characterized in that said derivative is combined, by weak bonds, with one or several hyaluronic acid calibrated fragments of molecular weight between 150 and 750 kDa.

According to a preferred embodiment of the invention, the molecular weight of these fragments is between 150 and 600 kDa, in a way even more preferred between 250 and 600 kDa.

By "organic silicon derivative", it is meant a compound defined by the following general formula (I):

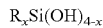

$$R_xSi(OH)_{4-x} \tag{I}$$

wherein:
R is a $(C_1-C_4)$alkyl,
x=1 and 2.

The organic silicon derivatives according to the invention are under the form of monomers, dimers or trimers, mainly monomers or dimers, or a mixture of monomers, dimers and trimers, mainly a mixture of monomers and dimers, with a state in solution which can be represented by the following formula (II):

$$[(T0)_R+(T1)_S+(T2)_T] \tag{II}$$

in which:
T0, T1 and T2 have respectively the formulas:

wherein:
R is such as above defined for compounds (I),
X represents a hydroxyl group or a radical R such as above defined, and
r, s and t are such as that $1 \le r+s+t \le 3$.

In the above formulas (I) and (II), it is meant by "$C_1-C_4$ alkyl group" a hydrocarbon chain having from 1 to 4 atoms of carbon, linear, ramified, or even cyclic. Such a group is notably a methyl, ethyl, propyl, butyl, 1-methylethyl, 1-methylpropyl, 2-methylpropyl, 1,1-dimethylethyl and cyclopropyl-methyl group.

By "fragments of hyaluronic acid", it is meant fragments resulting from native HA as such or from one of any of its salts, especially from sodium hyaluronate fragments.

According to an other advantageous embodiment of the invention, the organic silicon derivative of formula (I) is chosen among the monomethylsilanetriol or the dimethylsilanediol. It is especially chosen the monomethylsilanetriol, and even more particularly the monomethylsilanetriol combined with one or several hyaluronic acid fragments of molecular weight between 150 and 600 kDa (hereafter "MSH" complex) or between 250 and 600 kDa.

According to another aspect, the present invention also spreads to a cosmetic composition for topical application including, in association with any physiologically compatible excipient with skin, as main active ingredient, the complex such as previously defined, particularly the monomethylsilanetriol, and even more particularly the monomethylsilanetriol combined with one or several hyaluronic acid fragments of molecular weight between 150 and 600 kDa or between 250 and 600 kDa, said composition being intended for preventing or repairing the cutaneous damages related to aging for which it is necessary to boost the epidermal cell activity while limiting the catabolic action of the cutaneous tissue.

Advantageously, the quantity of complex of formula (I) in the above composition is between 1 and 10% in weight in relation to the total weight of the composition, preferably between 2 and 5% in weight.

One can mention, as an example of physiologically compatible excipient with skin, a tensioactive, a preservative, body fat, a dye, an emulsifier, a gelling agent, an emollient, a moisturizer, a pigment, an antioxidant or all other adjuvant usually used in cosmetics.

The compositions according to the invention are adapted to an administration through cutaneous topical way, presented under all forms usually used for such an administration. Advantageously, they are formulated for instance under the form of cream, milk, gel, lotion, emulsion, etc.

According to another aspect, the invention also concerns the use of a complex such as previously defined as a cytostimulating agent intended for boosting the epidermal cell (keratinocytes) activity while limiting the catabolic action of the cutaneous tissue. It is particularly used the monomethylsilanetriol, and even more particularly the monomethylsilanetriol combined with one or several hyaluronic acid fragments of molecular weight between 150 and 600 kDa or between 250 and 600 kDa.

Finally, according to a last aspect, the present invention concerns a cosmetic care process intended for preventing or repairing cutaneous damages related to aging and for which it is necessary to boost the epidermal cell activity. The process is achieved by applying on skin the composition such as previously defined, particularly based on the monomethylsilanetriol and even more particularly based on the monomethylsilanetriol combined with one or several hyaluronic acid fragments of molecular weight between 150 and 600 kDa or between 250 and 600 kDa.

As an illustration, it is hereafter mentioned two formulation examples of cosmetic composition according to the invention, successively with the monomethylsilanetriol combined with hyaluronic acid fragments of molecular weight between 150 and 600 kDa (formula A), and with the dimethylsilanediol combined with hyaluronic acid fragments of molecular weight between 250 and 600 kDa (formula B):

Formula A (cream)

| | |
|---|---|
| MSH complex (monomethylsilanetriol/HA fragments 150-600 kDa) | 5% |
| Hydrogenated polyisobutene | 7% |
| Isobutyl myristate | 3% |
| Cetyl Palmitate | 7% |
| Ethylene glycol monostearate | 5% |
| Sorbitan laurate | 2% |
| Polysorbate 20 | 2% |
| Carbomer (acrylate copolymer/acrylamide & mineral oil) | 0.3% |
| Phenoxyethanol | 0.5% |
| Water | qsp 100% |

Formula B (gel)

| | |
|---|---|
| Complex (dimethylsilanediol/HA fragments 250-600 kDa) | 5% |
| Carbomer (acrylate copolymer/acrylamide & mineral oil) | 1.5% |
| Sodium benzoate | 0.2% |
| Sorbic acid | 1% |
| 1,3-butanediol | 10% |
| Glycerine | 5% |
| Sodium carbonate | 0.13% |
| Phenoxyethanol | 0.9% |
| Water | qsp 100% |

As purely an indication, the invention is hereafter illustrated by the following tests above described in the specification (tests 1 to 3), and a comparative study (test 4). In tests 1, 2 and 4, the experimental studies have been carried out on a reconstructed human epidermis model (RHE, supplier: SkinEthic®) whose interest is a strong homology with human epidermis.

Test 1: evidence of the cytostimulating effect of the MSH complex on reconstructed epidermis with human origin.

The culture of RHE consisted in placing them in a "MCDB 153" growth medium (supplier : SkinEthic®) containing 5 mg/mL of insulin, 1.5 mM of $CaCl_2$ and 25 mg/ml of gentamycine, for 24 hours at 37° C. and 5% $CO_2$.

The observation of cellular proliferation is achieved with the immunotracking technique (Gerdes and al., Int. J. Cancer (1983), vol. 31, pp. 13-20) by using the "Ki67" cell proliferation tracer, for the three following configurations (after a 100 1 twice-daily deposit on RHE):
case 1: PBS buffer solution (control)
case 2: HA fragments 150-600 kDa (concentrations 2 and 5%)
case 3: MSH complex (concentrations 2 and 5%)

The obtained results are gathered in the hereafter table 1:

TABLE 1

| | concentration (%) | % cells expressing Ki67/ number of total cells (% in relation to the control) |
|---|---|---|
| case 1 (control) | — | — |
| case 2 (HAF 150-600 kDa) | 2.5 | 0 |
| case 2 (HAF 150-600 kDa) | 5 | +28 (±0.6) |
| case 3 (MSH complex) | 2.5 | +14 (±1.0) |
| case 3 (MSH complex) | 5 | +63 (±0.5) |

The results, taking values obtained from three independent experiments, underline a potentiated cytostimulation for the MSH complex according to the invention, because it is much higher to the one observed for the non combined fragmented HA.

Test 2: evidence of the absence of pro-inflammatory reply induction for the MSH complex The culture of RHE is identical to the one of the herebefore test 1. The dosage of the IL1 and IL8 pro-inflammatory interleukines is achieved on a supernatant resulting from culture medium after 24 hours of treatment, with the help of ELISA dosage kits (R&D System Quantikine Immunoassay, D800C, DTA00C and DLA50), and for identical configurations to those of the above test 1.

The obtained results are gathered in the hereafter table 2:

TABLE 2

| | concentration (%) | IL1α quantity (pg/ml) | IL8 quantity (pg/ml) |
|---|---|---|---|
| case 1 (control) | — | 1.8 (±0.1) | 38.8 (±11.5) |
| case 2 (HAF 150-600 kDa) | 2.5 | 1.4 (±0) | 40.2 (±4.9) |
| case 2 (HAF 150-600 kDa) | 5 | 0.6 (±0.3) | 31.0 (±0.6) |
| case 3 (MSH complex) | 2.5 | 3.5 (±1.8) | 20.1 (±7.2) |
| case 3 (MSH complex) | 5 | 3.4 (±0.8) | 34.8 (±13.7) |

No significant induction of pro-inflammatory cytokines is observed for the MSH complex according to the invention. It is even observed, in relation to the control as well as in relation to the non combined HA fragment, a reduction of the IL8 type-interleukines' rate.

Test 3: evidence of a slowed down catabolism on agarose gel for the MSH complex

The experimental study consisted in measuring the deterioration kinetic of the MSH complex according to the invention submitted in vitro to bovine hyaluronidases, by electrophoresis on agarose gel. 10 1 of 1 mg/ml hyaluronidases are mixed to 50 1 of complex in a PBS buffer solution during 30 minutes at 37° C.

Successively at 5, 15 and 30 minutes, 10 1 of reaction mixture are taken, then heated at 95° C. in order to stop the enzymatic reaction. These 10 1 are then deposited on an agarose gel and a suitable stain (Stains all®) is used for the electrophoresis disclosure.

As the agarose gel represented on the hereafter FIG. 1, the electrophoresis displays, for the three times of sampling and reaction, a more important distribution of HA with a high molecular weight for the MSH complex according to the invention, compared to fragmented HA non combined.

Test 4: comparison of cytostimulant effects of the MSH complex and of the dimethylsilanediol hyaluronate of high molecular weight Identically to the here-above test 1, keratinocytes' cellular proliferation is observed on reconstructed human epidermis RHE (with the immunotracking technique) for:
- the MSH complex according to the invention (based on 150-600 kDa HA fragments)
- the dimethylsilanediol hyaluronate marketed by the applicant under the "D.S.H. CN®" brand mark.
  D.S.H. CN® is an organo-silicon product resulting from the combination of dimethylsilanediol with hyaluronic acid of high molecular weight (1500 to 2200 kDa HA fragments).

The obtained results are gathered in the hereafter table 4, again in relation to a PBS buffer solution (control):

TABLE 4

| | concentration (%) | % cells expressing Ki67/ number of total cells (% in relation to the control) |
|---|---|---|
| control | — | — |
| D.S.H. CN ® | 5 | 0 (±2.2) |
| MSH complex | 5 | +69.5 (±3.1) |

What is claimed is:

1. A method of cosmetic care for repairing skin aging damage to a patient in need of boosting epidermal cell activity and limiting pro-inflammatory adverse effect of hyaluronic acid fragments produced by catabolic action of cutaneous tissue, the method comprising applying on a skin, a complex based on:
   an organic silicon derivative combined with
   one or several hyaluronic acid calibrated fragments of molecular weight between 150 and 600 kDa,
   said derivative being of formula (1):

$$R_xSi(OH)_{4-x} \quad (I),$$

wherein R is a $(C_1-C_4)$alkyl, and x=1 or 2.

2. The method according to claim 1, wherein said organic silicon derivative of formula (I) is selected from the group consisting of monomethylsilanetriol and dimethylsilanediol.

3. The method according to claim 1, wherein monomethylsilanetriol is combined with the one or several hyaluronic acid fragments of molecular weight between 150 and 600 kDa.

4. A method of cosmetic care for repairing skin aging damage to a patient in need of boosting the epidermal cell activity and limiting the pro-inflammatory adverse effect of hyaluronic acid fragments produced by catabolic action of cutaneous tissue, the method comprising applying on a skin, a composition comprising:
   i) a complex based on:
      an organic silicon derivative combined with
      one or several hyaluronic acid calibrated fragments of molecular weight between 150 and 600 kDa,
      said derivative being of formula (I):

$$R_xSi(OH)_{4-x} \quad (I)$$

wherein R is a $(C_1-C_4)$alkyl, and x=1 or 2, and
   ii) a physiologically compatible excipient with skin.

5. The method according to claim 4, wherein the concentration of said complex in the composition is between 2% and 5% in weight in relation to the total weight of the composition.

6. The method according to claim 4, wherein said physiologically compatible excipient with skin is selected from the group consisting of a preservative, a body fat, a dye, an emulsifier, a gelling agent, an emollient, a moisturizer, a pigment, and an antioxidant.

7. The method according to claim 6, wherein said physiologically compatible excipient with skin is selected from the group consisting of hydrogenated polyisobutene, isobutyl myristate, cetyl palmitate, ethylene glycol monostearate, sorbitan laurate, polysorbate 20, carbomer, phenoxyethanol, sodium benzoate, sorbic acid, 1,3-butanediol, glycerine, and sodium carbonate.

8. The method according to claim 4, wherein said composition is formulated in a form selected from the group consisting of a cream, a milk, a gel, a lotion, and an emulsion.

* * * * *